United States Patent

Hök

[11] 3,942,382
[45] Mar. 9, 1976

[54] PRESSURE TRANSDUCER

[75] Inventor: Bertil Hök, Uppsala, Sweden

[73] Assignee: Siemens Aktiengesellschaft, Erlangen, Germany

[22] Filed: Oct. 16, 1974

[21] Appl. No.: 515,682

[30] Foreign Application Priority Data
Oct. 18, 1973  Sweden............................ 7314083

[52] U.S. Cl. .................. 73/398 AR; 128/2.05 D
[51] Int. Cl.² ............................................ G01L 9/02
[58] Field of Search ....... 73/398 AR, 398 C, 398 R; 128/2.05 D, 2.07; 338/36, 38, 86

[56] References Cited
UNITED STATES PATENTS
2,566,369  9/1951  Putman.................................. 338/38
3,190,122  6/1965  Edwards............................ 73/398 C
3,496,775  2/1970  Sargent............................. 73/398 R

*Primary Examiner*—Donald O. Woodiel
*Attorney, Agent, or Firm*—Haseltine, Lake & Waters

[57] ABSTRACT

A pressure transducer including a measuring cell which is partly filled with a liquid and with the remainder being filled with a gas; a conduit filled with the liquid extending from the measuring cell, and which is open at an end thereof remote from the measuring cell; and means in the pressure transducer for generating an electrical value which corresponds to the particular gas volume.

9 Claims, 1 Drawing Figure

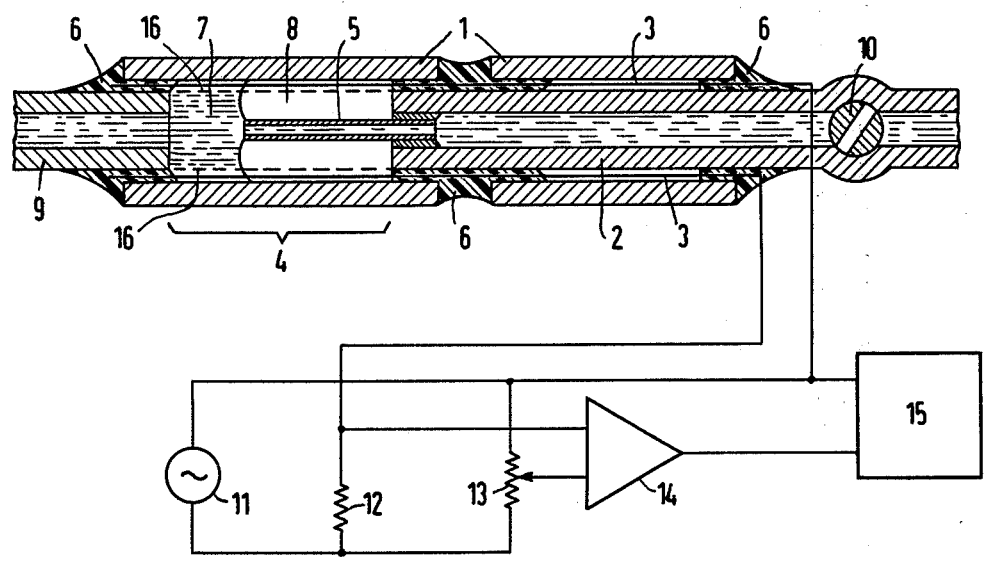

PRESSURE TRANSDUCER

FIELD OF THE INVENTION

The present invention relates to a pressure transducer and, more particularly, a pressure transducer for medical and physiological pressure measurements.

DISCUSSION OF THE PRIOR ART

Generally, as a rule, for medical and physiological pressure measurements there are employed liquid-filled plastic material catheters for the hydraulic transmission of the pressure signals from the region being measured to an externally located pressure transducer, the latter of which converts the liquid pressure into an electrical signal. The disadvantage of these measuring arrangements, however, consists of in that the electrical signal which is generated by the pressure transducer does not correspond precisely to the measured pressure due to inadequate transmission properties. On the basis of the foregoing, there have been developed presently miniature pressure transducers, which may be applied directly to the measuring region, for example, in a blood vessel. In an embodiment of that type of miniature pressure transducer, the movements of a membrane which is located within the tip of the catheter are sensed by strain gauges or indicators, for example, semiconductor elements, and converted into electrical signals. Notwithstanding the satisfactory results obtained, these pressure transducers have not found application in actual practice, since their costs are extremely high, and the introduction of electrically powered components in proximity to vital organs is connected with various risks to the patients.

SUMMARY OF THE INVENTION

Accordingly, it is an object of the present invention to provide a miniature pressure transducer having a construction which is extremely simple so as to become substantially less expensive in manufacture in comparison with previous transducers. Furthermore, during use of the inventive pressure transducer, the latter affords absolute safety to the patients.

The foregoing object is inventively achieved in that the pressure transducer includes a measuring cell which is partly filled with a liquid and with the remainder being filled with a gas; a conduit filled with the liquid extending from the measuring cell, and which is open at an end thereof remote from the measuring cell; and means in the pressure transducer for generating an electrical value which corresponds to the particular gas volume.

BRIEF DESCRIPTION OF THE DRAWING

Reference may now be had to the detailed description of an exemplary embodiment of a pressure transducer pursuant to the present invention, taken in conjunction with the sectional view shown in the single FIGURE of the accompanying drawing.

DETAILED DESCRIPTION

Referring now in detail to the FIGURE of the drawing, the pressure transducer is constituted of two concentrically positioned plastic material catheters 1 and 2, intermediate which there are located two platinum wires 3. The thinner or inner catheter 2 has one end surface thereof forming the boundary of a cylindrical chamber 4, the latter of which comprises the actual measuring cell.

A capillary tube 5 is sealingly connected with the catheter 2 so as to connect the inner space of the hollow catheter 2 with the inner space of the chamber 4, and extends into this chamber.

The catheter components are connected with each other by means of an epoxy resin 6 (ethoxylin resin) which also has a sealing function. When physiological saline solution 7 is sprayed through the thinner catheter 2 into the chamber 4, an air volume 8 is enclosed, and which extends from a connector 9 into the cylindrical chamber 4. When a cock 10 is subsequently closed, and the catheter with the open connector 9 thereof at its left-hand end introduced into a liquid vessel, for example, a blood vessel, the enclosed air volume 8 varies in accordance with Boyle-Mariottes' Law. The particular air volume thus corresponds to the pressure of the saline solution 7, and consequently to the pressure which is to be measured, and is converted into an electrical signal through intermediary of the platinum electrodes 3 which are located in a bridge provided for resistance measurement.

The resistance between the wires 3 is namely dependent upon the length of the column of the saline solution which borders the air volume 8. The resistance bridge 12, 13 is powered by means of an alternating current source 11 in order to avoid polarization of the electrodes 3. For receiving the output signals of the bridge 12, 13 there is utilized an amplifier 14. The electrical pressure signal is then further processed by an arrangement 15, for example, indicated. The dimensions of the transducer components 1 through 10 may be maintained extremely small. In an exemplary embodiment, the outer diameter thereof was 1.3 mm, and the length of the capillary tube 5 was 1.9 mm.

The pressure transducer distinguishes over most of the constructions described in publications in that it utilizes an enclosed elastic gas volume in lieu of a membrane. The advantage thereof is that a high degree of sensitivity may be attained on the basis of the elasticity of the gas volume, and the difficulty manufactured membrane attachment is eliminated.

For the exclusion of temperature influences due to the thermal expansion of the gas volume, the arrangement may be provided with a resistance which has a negative thermal coefficient. Since electrolytes, for example, saline solutions, belong to this type of resistance media, by employing an electrolyte of the above-described type there are obtained very good thermal operating properties. The electrolyte itself thus forms the resistance having negative thermal coefficients. The measured temperature influences are comparable with the best published values, approximately 0.5 mm Hg/°C.

The invention is not restricted to the utilization of an ohmic resistance variation for generation of the electrical pressure signal. Thus, for example, a capacitive pressure transducer can be formed, having the same construction as that above-described. The foregoing is achieved when the wires 3 in the measuring chamber 4 are insulated from the liquid 7 through the interposition of an insulating material cylinder 16. The insulating material cylinder 16 may be provided only for capacitive measurements, and consequently is shown in chaindotted representation. In this instance, the liquid must have a high specific resistance and a high dielectric value. The pressure variations are herein converted into changes in the capacitance between the electrodes 3. The temperature balance is present when the thermal dependency of the dielectric value of the liquid balances the thermal expansion of the gas.

Since Boyle-Mariottes' Law is a non-linear relationship, the indicator will evidence a particular non-linearity which, nevertheless, has a simple analytical formula.

$$u = \frac{\alpha + p}{1 + \beta \cdot p} \qquad (1);$$

wherein $u$ = the output voltage of the arrangement 15, $\alpha$ and $\beta$ = constants, and $p$ = the applied pressure. Measurements have shown that the above-mentioned function is valid with a degree of precision of better than ± 1% across that pressure range which comes into consideration for biomedical measurements.

The equation (1) can be employed in order to form a linearized supply circuit which will correct the non-linearity of the pressure transducer. Connected to the supply circuit may be a known analog multiplier, which is employed for the purpose of dividing the output voltage which is received from the arrangement 15 with the difference between an adjustable constant voltage and the output voltage. After this arithmetic mathematical operation which may be carried out in an analog form, there is received an output signal which, with respect to the applied pressure, is linear at a precision which is better than ± 2%. The arithmetic mathematical operations may also be carried out with a corresponding digital arrangement.

The hydrodynamic expansibility of the pressure transducer, as well as the inertia and viscosity of the liquid column, determine the dynamic properties of the system. Through experiments with rapid pressure variations it has been ascertained that the pressure transducer with the described measurements evidences a resonance frequency which lies at about 95 Hz at an attenuation factor of 0.5. At a further reduction of the measurements, the resonance frequency is significantly increased.

The construction of the pressure transducer system may be varied within the scope of the invention, depending upon the degree of safety which is required for the measurement. It is suitable that the pressure transducer be galvanically protected from ground, so as to prevent leakage current. This may be effected by means of, for example, known insulating amplifiers, which facilitate the control of a power operated recorder or the like by the pressure signal.

The exemplary embodiment requires very little energy, so that an energy source which is insulated from ground, for example, a battery, may be employed without difficulty when a DC/AC converter is associated therewith. The input voltage of the resistance bridge should have a low amplitude, approximately 100 mV, and a relatively high frequency, approximately 25 kHz.

While there has been shown what is considered to be the preferred embodiment of the invention, it will be obvious that modifications may be made which come within the scope of the disclosure of the specification.

What is claimed is:

1. A pressure transducer for generating an electrical signal in conformance with a liquid pressure, said transducer comprising a measuring cell including a chamber partly filled with a liquid and the remaining part thereof with a gas entrapped in said chamber; a conduit filled with said liquid having one end thereof communicating with the liquid-filled part of the chamber of said measuring cell, said conduit having an open end remote from said measuring cell communicating with a fluid-filled vessel for measurement of the fluid pressure in the latter; tube means extending into said chamber connected to a source for supplying quantities of said liquid to said chamber; valve means for selectively restricting flow of liquid from said liquid supply source and for sealing said tube means, said gas volume in said chamber being varied responsive to the fluid pressure in said fluid vessel acting on the liquid in said conduit; and means in said transducer for generating an electrical value of a magnitude in conformance with the particular gas volume.

2. A pressure transducer as claimed in claim 1, comprising a thermally dependent resistance adapted to influence the electrical signal in conformance with the particular temperature in said measuring cell.

3. A pressure transducer as claimed in claim 1, said liquid in said measuring cell comprising an electrolyte.

4. A pressure transducer as claimed in claim 3, said liquid comprising physiological saline solution.

5. A pressure transducer as claimed in claim 3, comprising two electrodes extending into said liquid; and a circuit arrangement connected to said electrodes for measuring the particular ohmic resistance between said two electrodes.

6. A pressure transducer as claimed in claim 5, said electrodes being constituted of platinum.

7. A pressure transducer as claimed in claim 1, comprising two condensor layers being located interiorly of said transducer; and means insulating said condensor layers from said liquid, said condensor layers being positioned so that the quantity of liquid therebetween varies in conformance with the pressure being measured.

8. A pressure transducer as claimed in claim 5, said liquid in said measuring cell having the thermal coefficient for the specific resistance thereof selected so as to eliminate temperature influences on said gas volume.

9. A pressure transducer as claimed in claim 7, said liquid in said measuring cell having the specific dielectric value thereof selected so as to eliminate temperature influences on said gas volume in said measuring cell.

* * * * *